US009636659B2

(12) United States Patent
Cheung et al.

(10) Patent No.: US 9,636,659 B2
(45) Date of Patent: *May 2, 2017

(54) SELECTIVE HYDROGENATION CATALYST AND METHODS OF MAKING AND USING SAME

(71) Applicant: Chevron Phillips Chemical Company LP, The Woodlands, TX (US)

(72) Inventors: Tin-Tack Peter Cheung, Kingwood, TX (US); Joseph Bergmeister, III, Kingwood, TX (US); Stephen L. Kelly, Kingwood, TX (US)

(73) Assignee: Chevron Phillips Chemical Company LP, The Woodlands, TX (US)

(*) Notice: Subject to any disclaimer, the term of this patent is extended or adjusted under 35 U.S.C. 154(b) by 0 days.

This patent is subject to a terminal disclaimer.

(21) Appl. No.: 14/799,440

(22) Filed: Jul. 14, 2015

(65) Prior Publication Data

US 2015/0314270 A1   Nov. 5, 2015

Related U.S. Application Data

(63) Continuation of application No. 14/224,887, filed on Mar. 25, 2014, now Pat. No. 9,144,787, which is a continuation of application No. 13/414,544, filed on Mar. 7, 2012, now Pat. No. 9,108,188.

(51) Int. Cl.
| | | |
|---|---|---|
| *B01J 23/00* | (2006.01) | |
| *B01J 23/50* | (2006.01) | |
| *B01J 35/10* | (2006.01) | |
| *B01J 37/08* | (2006.01) | |
| *B01J 37/18* | (2006.01) | |
| *B01J 37/24* | (2006.01) | |
| *B01J 21/04* | (2006.01) | |
| *B01J 23/44* | (2006.01) | |
| *B01J 37/00* | (2006.01) | |
| *C07C 7/167* | (2006.01) | |
| *C07C 5/08* | (2006.01) | |
| *C07C 5/09* | (2006.01) | |

(52) U.S. Cl.
CPC .............. *B01J 23/50* (2013.01); *B01J 21/04* (2013.01); *B01J 23/005* (2013.01); *B01J 23/44* (2013.01); *B01J 35/109* (2013.01); *B01J 35/1009* (2013.01); *B01J 35/1014* (2013.01); *B01J 35/1038* (2013.01); *B01J 35/1042* (2013.01); *B01J 35/1061* (2013.01); *B01J 35/1066* (2013.01); *B01J 35/1071* (2013.01); *B01J 35/1076* (2013.01); *B01J 37/0009* (2013.01); *B01J 37/08* (2013.01); *B01J 37/18* (2013.01); *B01J 37/24* (2013.01); *C07C 5/08* (2013.01); *C07C 5/09* (2013.01); *C07C 7/167* (2013.01); *Y02P 20/52* (2015.11)

(58) Field of Classification Search
None
See application file for complete search history.

(56) References Cited

U.S. PATENT DOCUMENTS

| | | | |
|---|---|---|---|
| 3,679,762 A | 7/1972 | La Hue et al. | |
| 3,770,617 A | 11/1973 | Riley et al. | |
| 3,898,155 A | 8/1975 | Wilson | |
| 3,898,322 A | 8/1975 | Leach | |
| 4,115,248 A | 9/1978 | Mulaskey | |
| 4,257,877 A | 3/1981 | Mahendroo | |
| 4,301,037 A | 11/1981 | Sanchez et al. | |
| 4,404,124 A | 9/1983 | Johnson et al. | |
| 4,410,715 A | 10/1983 | McMullen et al. | |
| 4,484,015 A | 11/1984 | Johnson et al. | |
| 4,499,203 A | 2/1985 | Toulhoat et al. | |
| 4,762,956 A | 8/1988 | Liu et al. | |
| 5,057,481 A | 10/1991 | Bhasin | |
| 5,514,362 A | 5/1996 | Miller | |
| 5,558,851 A | 9/1996 | Miller | |
| 5,935,897 A | 8/1999 | Trübenbach et al. | |
| 6,417,136 B2 | 7/2002 | Cheung et al. | |
| 6,573,214 B2 | 6/2003 | Abdo et al. | |
| 6,600,056 B1 | 7/2003 | Mikawa et al. | |

(Continued)

FOREIGN PATENT DOCUMENTS

| | | |
|---|---|---|
| CA | 2576964 C | 3/2012 |
| CN | 1361231 A | 7/2002 |

(Continued)

OTHER PUBLICATIONS

English translation of Chinese Patent Publication No. 101433842A, published on May 20, 2009, 16 pages.
Foreign communication from a related counterpart application—International Preliminary Report on Patentability, PCT/US2013/058514, Mar. 8, 2016, 15 pages.
Alerasool, Saeed, "Emerging Trends in Industrial Catalysis," Catalysis Club of Chicago, Apr. 4, 2005, pp. 1-69, Engelhard Corporation.
Che, Chunxia, et al., "C2 front-end hydrogenation catalyst and preparation method," machine translation of Chinese Patent Publication No. 102989453, published on Mar. 27, 2013, 17 pages.
Database WPI/Thomson Scientific, Week 201360, XP-002721624, abstract of CN102989453, 2 pages.
English Translation of Chinese Patent Publication No. 1361231A, 11 pages.
English Translation of Chinese Patent Publication No. 1364855A, 26 pages.
English Translation of Chinese Patent Publication No. 102989453A, 28 pages.

(Continued)

*Primary Examiner* — Colin W Slifka
(74) *Attorney, Agent, or Firm* — Conley Rose, P.C.; Rodney B. Carroll; Lynda S. Jolly

(57) ABSTRACT

A composition comprising an extruded inorganic support comprising an oxide of a metal or metalloid, and at least one catalytically active metal, wherein the extruded inorganic support has pores, a total pore volume, and a pore size distribution, wherein the pore size distribution displays at least two peaks of pore diameters, each peak having a maximum, wherein a first peak has a first maximum of pore diameters of equal to or greater than about 120 nm and a second peak has a second maximum of pore diameters of less than about 120 nm, and wherein greater than or equal to about 5% of a total pore volume of the extruded inorganic support is contained within the first peak of pore diameters.

23 Claims, 5 Drawing Sheets

(56) References Cited

U.S. PATENT DOCUMENTS

| | | | |
|---|---|---|---|
| 6,627,778 | B2 | 9/2003 | Xu et al. |
| 6,797,669 | B2 | 9/2004 | Zhang et al. |
| 6,984,310 | B2 | 1/2006 | Ginestra et al. |
| 7,186,757 | B2 | 3/2007 | Espinoza et al. |
| 7,301,062 | B2 | 11/2007 | Gartside et al. |
| 7,319,176 | B2 | 1/2008 | Ryu et al. |
| 7,417,007 | B2 | 8/2008 | Cheung et al. |
| 7,560,577 | B2 | 7/2009 | Hirota et al. |
| 7,638,455 | B2 | 12/2009 | Birke et al. |
| 7,745,370 | B2 | 6/2010 | Blankenship et al. |
| 7,932,408 | B2 | 4/2011 | Gückel |
| 7,977,274 | B2 | 7/2011 | Gueckel |
| 8,067,334 | B2 | 11/2011 | Hill et al. |
| 8,633,127 | B2 | 1/2014 | Cheung et al. |
| 9,108,188 | B2 | 8/2015 | Cheung et al. |
| 9,144,787 | B2 | 9/2015 | Cheung et al. |
| 2001/0001805 | A1 | 5/2001 | Brown et al. |
| 2003/0134744 | A1 | 7/2003 | Blankenship et al. |
| 2004/0192983 | A1 | 9/2004 | Bergmeister et al. |
| 2009/0030250 | A1* | 1/2009 | Hill .................. C10G 45/40 585/273 |
| 2014/0005449 | A1 | 1/2014 | Cheung et al. |

FOREIGN PATENT DOCUMENTS

| | | |
|---|---|---|
| CN | 1364855 A | 8/2002 |
| CN | 101072637 A | 11/2007 |
| CN | 101433842 A | 5/2009 |
| CN | 102989453 A | 3/2013 |
| EP | 1852184 A1 | 11/2007 |
| EP | 2570470 A1 | 3/2013 |
| JP | S595946 A | 1/1984 |
| JP | S596946 A | 1/1984 |
| JP | H01254254 A | 10/1989 |
| JP | H0416572 A | 1/1992 |
| JP | 2006181562 A | 7/2006 |
| JP | 2008086877 A | 4/2008 |
| JP | 2008515631 A | 5/2008 |
| JP | 2008212798 A | 9/2008 |
| JP | 2009529405 A | 8/2009 |
| JP | 2013091010 A | 5/2013 |
| WO | 0119763 A1 | 3/2001 |
| WO | 0141923 A1 | 6/2001 |
| WO | 2006019717 A1 | 2/2006 |
| WO | 2012140617 A1 | 10/2012 |
| WO | 2013134065 A2 | 9/2013 |
| WO | 2013134065 A3 | 9/2013 |
| WO | 2015034521 A1 | 3/2015 |

OTHER PUBLICATIONS

Ertl, G., et al., "Handbook of Heterogeneous Catalysis," 1997, vol. 2, Chapter 3: Characterization of Solid Catalysts, pp. 427-440 plus 5 pages cover page, publishing information, foreword, outline, and contents, VCH Verlagsgesellschaft mbH, Weinheim.

Feng, Jun-Ting, et al., "Catalytic hydrogenation of ethylanthraquinone over highly dispersed eggshell Pd/SiO$_2$-Al$_2$O$_3$ spherical catalysts," Applied Catalysis A: General, 2010, pp. 240-245, vol. 382, Elsevier B.V.

Foreign communication from a related counterpart application—Invitation to Pay Additional Fees, PCT/US2013/028597, Jun. 25, 2013, 6 pages.

Foreign communication from a related counterpart application—International Search Report and Written Opinion, PCT/US2013/028597, Sep. 16, 2013, 19 pages.

Foreign communication from a related counterpart application—International Preliminary Report on Patentability, PCT/US2013/028597, Sep. 9, 2014, 13 pages.

Foreign communication from a related counterpart application—Invitation to Pay Additional Fees, PCT/US2013/058514, Mar. 25, 2014, 11 pages.

Foreign communication from a related counterpart application—International Search Report and Written Opinion, PCT/US2013/058514, Jun. 17, 2014, 22 pages.

Nilsson, Marita, et al., "Catalytic properties of PD supported on ZnO/ZnAl$_2$O$_4$/Al$_2$O$_3$ mixtures in dimethyl ether autothermal reforming," Applied Catalysis B: Enviromental, 2009, pp. 18-26, vol. 86, Elsevier B.V.

Office Action dated May 19, 2014 (49 pages), U.S. Appl. No. 14/020,442 filed Sep. 6, 2013.

Office Action (Final) dated Nov. 5, 2014 (24 pages), U.S. Appl. No. 14/020,442, filed Sep. 6, 2013.

Office Action dated Mar. 20, 2015 (19 pages), U.S. Appl. No. 14/020,442, filed Sep. 6, 2013.

Office Action (Final) dated Jun. 29, 2015 (10 pages), U.S. Appl. No. 14/020,442, filed Sep. 6, 2013.

Satterfield, Charles N., et al., "Diffusion in commercially manufactured pelleted catalysts," I&EC Process Design and Development, Apr. 1968, pp. 256-260, vol. 7, No. 2.

Specification for patent application entitled "Selective Hydrogenation Catalyst and Methods of Making and Using Same," by Tin-Tack Peter Cheung, et al., filed Dec. 29, 2015 as U.S. Appl. No. 14/982,310.

Tao, Kai, et al., "Chemical and spatial promotional effects of bimodal pore catalysts for methane dry reforming," Chemical Engineering Journal, 2011, pp. 258-263, vol. 170, Elsevier B.V.

Zhang, Yi, et al., "Multi-functional alumina-silica bimodal pore catalyst and its application for Fischer-Tropsch synthesis," Applied Catalysis A: General, 2005, pp. 252-258, vol. 292, Elsevier B.V.

Catalysis Society of Japan, "Hydrotreating Process," May 20, 1998, pp. 46-48 (7 pages), Japan Petroleum Institute.

Kabe, T., "Hydrorefining—Science & Technology," Oct. 20, 2000, pp. 342-343 (4 pages), IPC Co., Ltd.

Koza, S., "Catalysis Design," Catalysis Lectures, Catalysis Society of Japan, Dec. 10, 1985, vol. 5, (Engineering vol. 1), p. 94 (6 pages), NOMA,Tadanichi.

Koza, S., "Catalysis Design," Catalysis Lectures, Catalysis Society of Japan, Jul. 10, 1985, vol. 7, (Industrial Catalytic Reactions vol. 1), pp. 52-54 (10 pages), NOMA,Tadanichi.

Tanabe, K., "Metal Oxides and Composite Oxides," Aug. 10, 1991, pp. 72-74 (5 pages), Sawako NOMA, Lodansha, Ltd.

Foreign communication from a related application—JP2014-560979, Office Action, Dec. 16, 2016, 4 pages.

Foreign communication from a related application—JP2014-560979, Third Party Observation, Dec. 16, 2016, 45 pages.

Foreign communication from a related application—JP2016-540861, Third Party Observation, Jan. 20, 2017, 59 pages.

Foreign communication from a related counterpart application—Office Action, Taiwan Application No. 102132358, Jan. 4, 2017, 13 pages.

* cited by examiner

SELECTIVE HYDROGENATION CATALYST AND METHODS OF MAKING AND USING SAME

CROSS-REFERENCE TO RELATED APPLICATION

This application is a continuation of and claims priority to U.S. patent application Ser. No. 14/224,887 filed Mar. 25, 2014, published as US2014/0206916 A1, which is a continuation of U.S. patent application Ser. No. 13/414,544 filed Mar. 7, 2012, published as US 2013/0237729 A1, both entitled "Selective Hydrogenation Catalyst and Methods of Making and Using Same," each of which is incorporated herein by reference in its entirety.

STATEMENT REGARDING FEDERALLY SPONSORED RESEARCH OR DEVELOPMENT

Not applicable.

REFERENCE TO A MICROFICHE APPENDIX

Not applicable.

BACKGROUND

Technical Field

The present disclosure relates to the production of unsaturated hydrocarbons, and more particularly to a selective hydrogenation catalyst and methods of making and using same.

Background

Unsaturated hydrocarbons such as ethylene and propylene are often employed as feedstocks in preparing value added chemicals and polymers. Unsaturated hydrocarbons can be produced by pyrolysis or steam cracking of hydrocarbons including hydrocarbons derived from coal, hydrocarbons derived from synthetic crude, naphthas, refinery gases, ethane, propane, butane, and the like. Unsaturated hydrocarbons produced in these manners usually contain small proportions of highly unsaturated hydrocarbons such as acetylenes and diolefins that can adversely affect the production of subsequent chemicals and polymers. Thus, to form an unsaturated hydrocarbon product such as a polymer grade monoolefin, the amount of acetylenes and diolefins in the monoolefin stream is typically reduced. For example, in polymer grade ethylene, the acetylene content typically is less than about 2 ppm.

One technique commonly used to reduce the amount of acetylenes and diolefins in an unsaturated hydrocarbon stream primarily comprising monoolefins involves selectively hydrogenating the acetylenes and diolefins to monoolefins. This process is selective in that hydrogenation of the monoolefin and the highly unsaturated hydrocarbons to saturated hydrocarbons is minimized. For example, the hydrogenation of ethylene or acetylene to ethane is minimized. An ongoing need exists for improved selective hydrogenation catalysts.

SUMMARY

Disclosed herein is a composition comprising an extruded inorganic support comprising an oxide of a metal or metalloid, and at least one catalytically active metal, wherein the extruded inorganic support has pores, a total pore volume, and a pore size distribution, wherein the pore size distribution displays at least two peaks of pore diameters, each peak having a maximum, wherein a first peak has a first maximum of pore diameters of equal to or greater than about 120 nm and a second peak has a second maximum of pore diameters of less than about 120 nm, and wherein greater than or equal to about 5% of a total pore volume of the extruded inorganic support is contained within the first peak of pore diameters.

Also disclosed herein is a method of preparing a hydrogenation catalyst comprising extruding a mixture comprising an oxide of a metal or metalloid, a pore former, and water to form an extrudate, drying the extrudate to form a dried extrudate, calcining the dried extrudate to from a calcined extrudate, contacting the calcined extrudate with a chlorine-containing compound to form a chlorided support, reducing the amount of chloride in the chlorided support to form a cleaned chlorided support, and contacting the cleaned chlorided support with a Group 10 metal and a Group 1B metal to form a hydrogenation catalyst, wherein a pore size distribution for the hydrogenation catalyst displays at least two peaks of pore diameters, each peak having a maximum, and wherein a first peak has a first maximum of pore diameters that is equal to or greater than about 120 nm and a second peak has a second maximum of pore diameters that is less than about 120 nm.

Further disclosed herein is an extruded inorganic support comprising an oxide of a metal or metalloid, wherein the extruded inorganic support displays a pore size distribution for at least two peaks of pore diameters, each peak having a maximum, wherein a first peak has a first maximum of pore diameters of equal to or greater than about 120 nm and a second peak has a second maximum of pore diameters of less than about 120 nm, wherein greater than or equal to 15% of a total pore volume of the extruded inorganic support is contained within the first peak of pore diameters, and wherein the inorganic support has a surface area of from about 5 $m^2/g$ to about 15 $m^2/g$.

Further disclosed herein is a method of preparing a hydrogenation catalyst comprising selecting an inorganic support having a multimodal distribution of pore diameters, wherein at least one distribution of pore diameters comprises pores having a diameter of equal to or greater than about 120 nm, extruding a mixture comprising the inorganic support and water to form an extrudate, drying the extrudate to form a dried extrudate, calcining the dried extrudate to from a calcined extrudate, and contacting the calcined extrudate with a Group VIII metal and a Group 1B metal to form a hydrogenation catalyst.

Further disclosed herein is a method comprising preparing a plurality of extruded inorganic supports consisting essentially of silica, titania, alumina, or a spinel, plotting the pore diameter as a function of a log of differential mercury intrusion for the extruded inorganic support, and identifying the extruded inorganic supports having at least two peaks, each peak having a maximum, wherein a first peak comprises pores with a first pore diameter maximum equal to or greater than about 120 nm, and wherein the first peak of pore diameters represents greater than or equal to about 5% of a total pore volume of the extruded inorganic support.

BRIEF DESCRIPTION OF THE DRAWINGS

For a more complete understanding of the present disclosure and the advantages thereof, reference is now made to the following brief description, taken in connection with the accompanying drawings and detailed description, wherein like reference numerals represent like parts.

DETAILED DESCRIPTION

Figure 1:
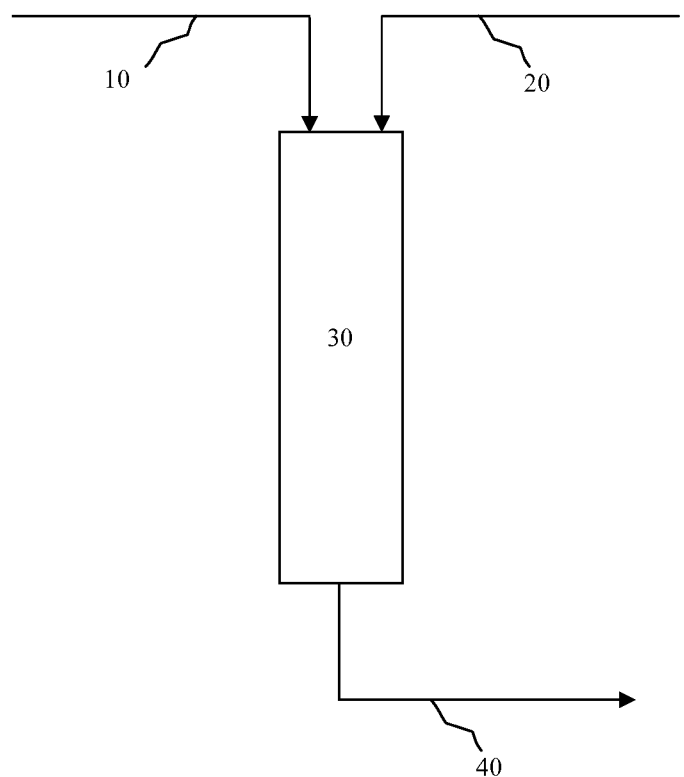
FIG. 1 depicts a process flow diagram of an embodiment of a selective hydrogenation process.
Figure 2:
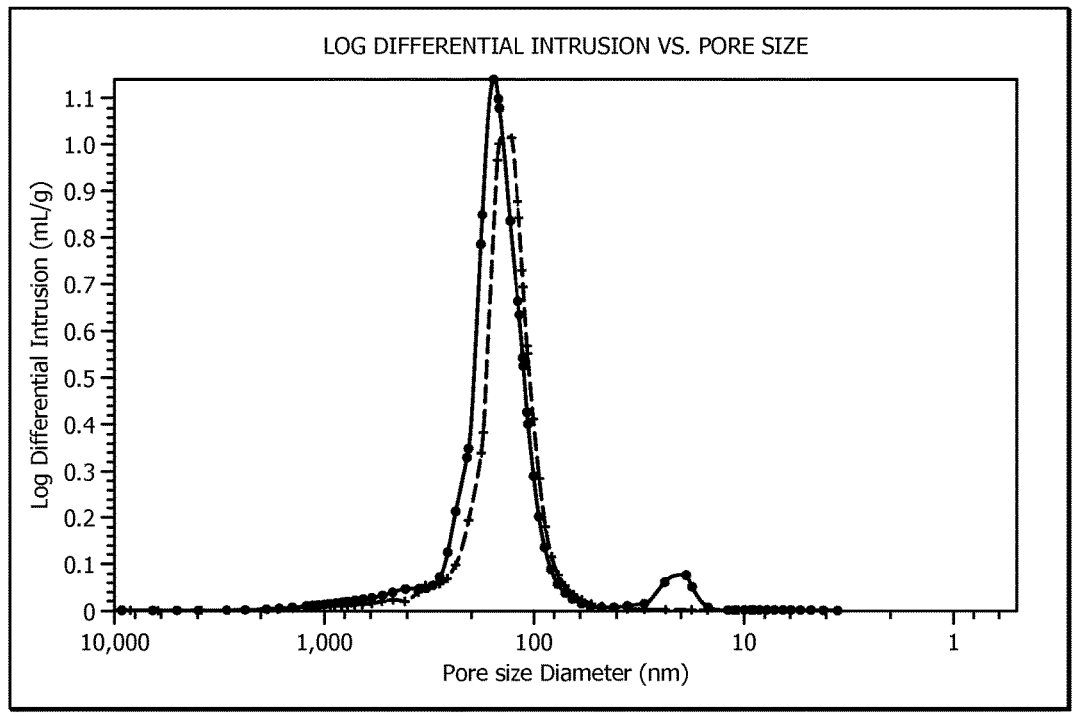
FIGS. 2-6 are plots of the log of differential mercury intrusion as a function of pore size diameter for the samples from Example 1.
Figure 3:
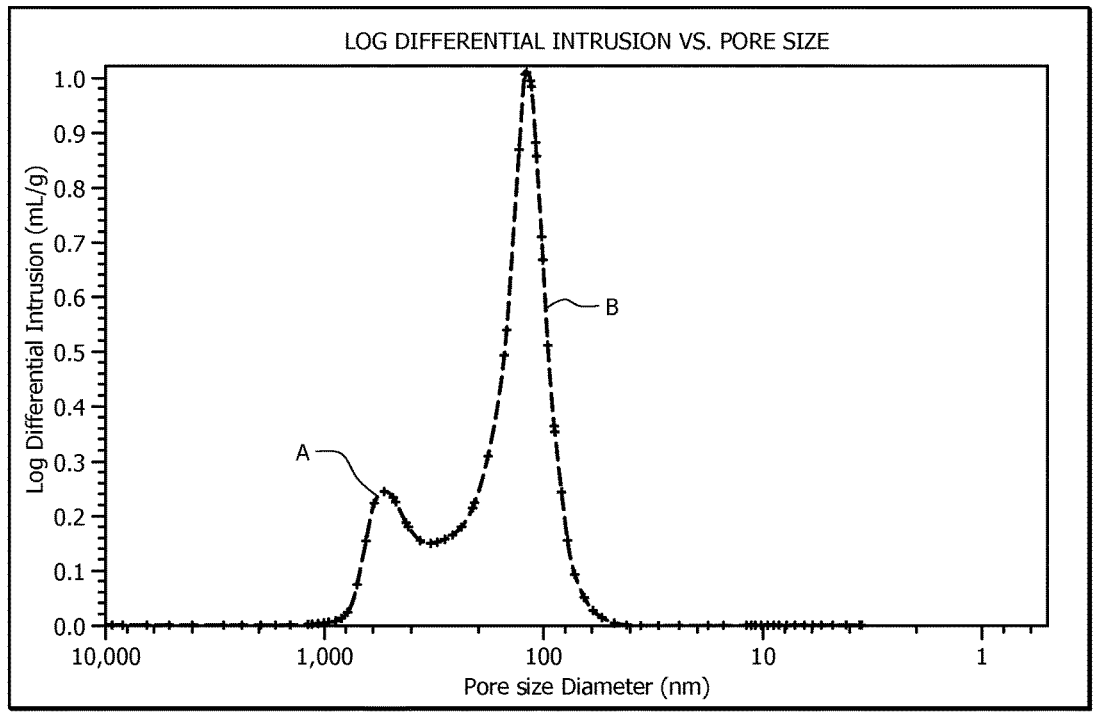
Figure 4:
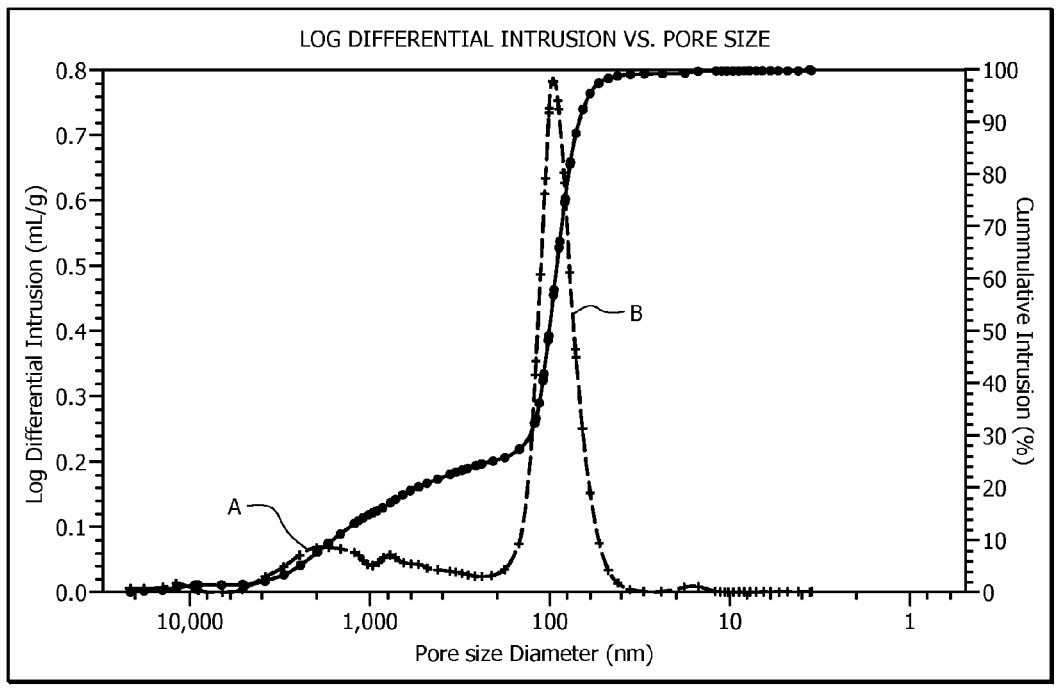
Figure 5:
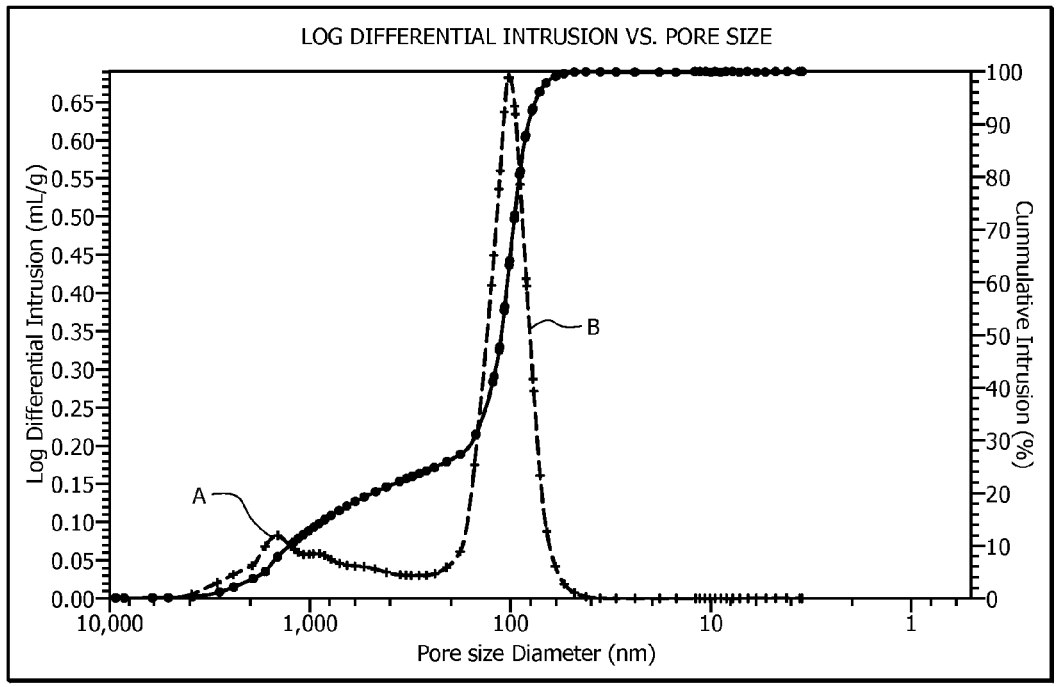
Figure 6:
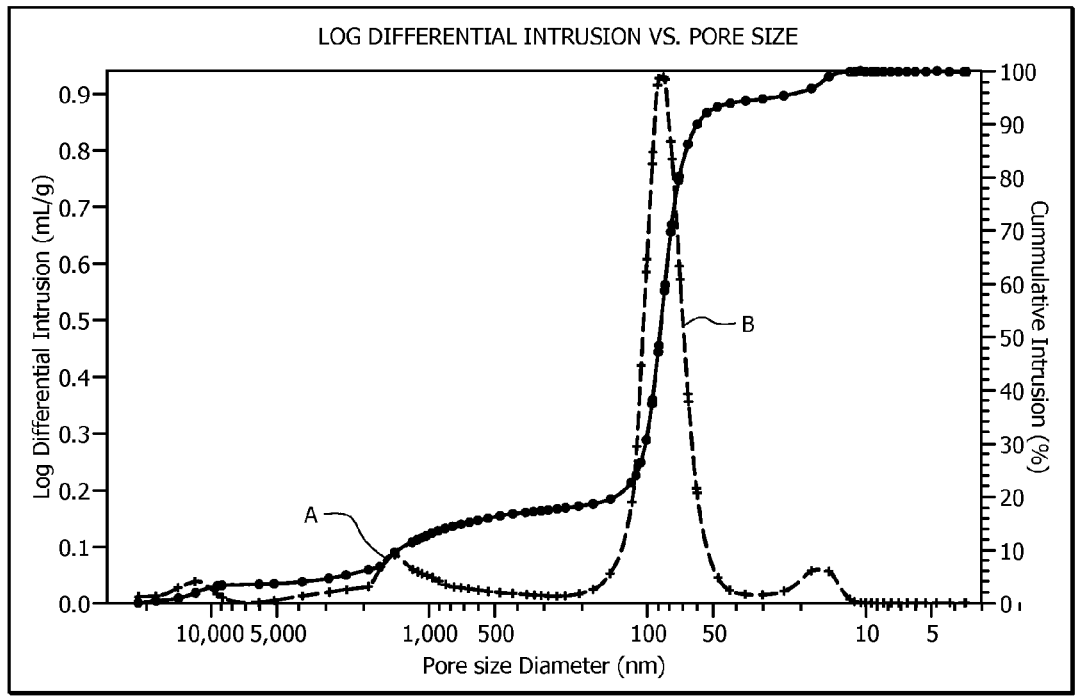

It should be understood at the outset that although an illustrative implementation of one or more embodiments are provided below, the disclosed systems and/or methods can be implemented using any number of techniques, whether currently known or in existence. The disclosure should in no way be limited to the illustrative implementations, drawings, and techniques illustrated below, including the exemplary designs and implementations illustrated and described herein, but can be modified within the scope of the appended claims along with their full scope of equivalents.

Disclosed herein are hydrogenation catalysts comprising a Group 10 metal and a catalyst support. In an embodiment the catalyst support comprises an oxide of a metal or metalloid and displays a characteristic pore size distribution. Catalysts of the type disclosed herein can display a hydrogenation selectivity that remains stable over a longer time period as will be described in more detail later herein.

In an embodiment, the catalyst comprises a support of an oxide of a metal or metalloid. In an embodiment, the catalyst support comprises silica, titania, alumina, aluminate, or combinations thereof. Alternatively, the catalyst support consists or consists essentially of silica, titania, alumina, aluminate, or combinations thereof. In an embodiment, the catalyst support comprises a spinel. Alternatively, the catalyst support consists or consists essentially of a spinel. Herein, a spinel refers to any of a class of minerals of general formulation $A^{2+}B_2^{3+}O_4^{2-}$ which crystallize in the cubic (isometric) crystal system, with the oxide anions arranged in a cubic, close-packed lattice and the cations A and B occupying some or all of the octahedral and tetrahedral sites in the lattice. Nonlimiting examples of materials suitable for use in the catalyst supports of this disclosure include aluminas, silicas, titanias, zirconias, aluminosilicates (e.g., clays, ceramics, and/or zeolites), spinels (e.g., zinc aluminate, zinc titanate, and/or magnesium aluminate), or combinations thereof.

In an embodiment, the catalyst support comprises an alumina. Alternatively the catalyst support consists or consists essentially of an alumina. For example, the catalyst support can comprise, consist of, or consist essentially of an alpha ($\alpha$)-alumina support. The $\alpha$-alumina support can be prepared using any suitable methodology. The alumina support can include additional components that do not adversely affect the catalyst such as zirconia, silica, thoria, magnesia, fluoride, sulfate, phosphate, or mixtures thereof.

The catalyst support can have a surface area of from about 1 square meters per gram ($m^2/g$), to about 35 $m^2/g$, or alternatively of from about 3 $m^2/g$ to about 25 $m^2/g$, or alternatively of from about 5 $m^2/g$ to about 15 $m^2/g$. The surface area of the support can be determined using any suitable method. An example of a suitable method for determining the surface area of the support includes the Brunauer, Emmett, and Teller ("BET") method, which measures the quantity of nitrogen adsorbed on the support.

In an embodiment, a catalyst support of the type disclosed herein is further characterized by a total pore volume as measured by differential mercury intrusion in the range of from about 0.1 cc/g to about 0.6 cc/g, alternatively from about 0.2 cc/g to about 0.55 cc/g. The pore volume of the support can be measured by a differential mercury intrusion method such as is described in ASTM UOP578-02, entitled "Automated Pore Volume and Pore Size Distribution of Porous Substances by Mercury Porosimetry," which is incorporated herein by reference in its entirety.

In an embodiment the catalyst support, the resultant catalyst, or both of the type disclosed herein displays a plot of the pore diameter on a logarithmic axis as a function of a log of differential mercury intrusion having two to four peaks corresponding to the presence of at least two to four distributions of pore diameters. Hereinafter, a plot of the pore diameter on a logarithmic axis as a function of a log of differential mercury intrusion is referred to as the pore size distribution.

In an embodiment, a catalyst support, the resultant catalyst, or both of the type disclosed herein is further characterized by an at least bimodal pore size distribution. In an embodiment a catalyst support, the resultant catalyst, or both of the type disclosed herein displays a pore size distribution having at least two peaks corresponding to the presence of at least two distributions of pore diameters. The first peak, designated peak A, corresponds to distribution A and can have a first maximum of pore diameters equal to or greater than about 120 nm. For example, peak A can have a maximum of pore diameters of from about 200 nm to about 9000 nm, alternatively from about 400 nm to about 8000 nm, or alternatively from about 600 to about 6000.

The second peak, designated peak B, corresponds to distribution B and can have a second maximum of pore diameters of less than about 120 nm. For example, peak B can have a maximum of pore diameters of from about 15 nm to less than about 120 nm, alternatively from about 115 nm to about 25 nm, or alternatively from about 115 nm to about 30 nm. Examples of peak A and peak B are identified in FIGS. 3-6.

In an embodiment, the distance between the maximum of peak A and the maximum of peak B is at least about 400 nm, alternatively at least 500 nm, alternatively from about 400 nm to about 3900 nm, or alternatively from about 400 nm to about 2900 nm. In an embodiment peak A, peak B, or both is non-Gaussian. In an embodiment, peak A is non-Gaussian and displays a peak width at half height that is greater than the peak width at half height of peak B.

In an embodiment greater than or equal to about 5% of the total pore volume of the catalyst support, the resultant catalyst, or both is contained within peak A, alternatively greater than or equal to about 10% of the total pore volume of the catalyst support is contained within peak A, or alternatively greater than or equal to about 15% of the total pore volume of the catalyst support is contained within peak A. In an embodiment from about 5% to about 75% of the total pore volume of the catalyst support, the resultant catalyst, or both is contained within peak A, alternatively from about 10% to about 60% of the total pore volume of the catalyst support is contained within peak A, or alternatively from about 15% to about 40% of the total pore volume of the catalyst support is contained within peak A. In an embodiment less than or equal to about 95% of the total pore volume of the catalyst support, the resultant catalyst, or both is contained within peak B, alternatively less than or equal to about 90%, alternatively less than or equal to about 85%. In an embodiment from about 95% to about 25% of the total pore volume of the catalyst support, the resultant catalyst, or both is contained within peak B, alternatively from about 90% to about 40% of the total pore volume of the catalyst support is contained within peak B, or alternatively from about 85% to about 60% of the total pore volume of the catalyst support is contained within peak B.

In an embodiment, a catalyst support of the type disclosed herein is formed from a mixture comprising an oxide of a metal or metalloid, a pore former, and water which are contacted to form an extrudate. The mixture can also include a pore former (also known as a pore generator) which can be any compound that can be mixed with the above components and that is combustible upon heating thereby producing voids. This pore generator helps to maintain and/or increase the porosity of the catalyst support composition. Examples of such pore generators include, but are not limited to, cellulose, cellulose gel, microcrystalline cellulose, methyl cellulose, zinc stearate, flours, starches, modified starches, graphite, polymers, carbonates, bicarbonates, microcrystalline wax, or mixtures thereof. The amount of the pore generator component used in this disclosure is in the range of about 0.1 to about 25 weight percent (wt. %) based on the total weight of the components (1.1-1.5). Alternatively, the amount ranges from about 1 wt. % to about 10 wt. % alternatively from about 3 wt. % to about 6 wt. %. Variation in raw materials, such as particle size and particle morphology of the alumina used, can impact porosity and pore size distribution.

In an embodiment, the mixture can be formed into any suitable shape. Methods for shaping particles include, for example, extrusion, spray drying, pelletizing, agglomeration, oil drop, and the like. In an embodiment, the mixture is formed into an extrudate, for example as described in U.S. Pat. Nos. 5,558,851 and 5,514,362, each of which are incorporated herein in their entirety. In an embodiment, the mixture further comprises an extrusion aid. An extrusion aid can function to improve the rheology of the mixture. This improvement in the rheology of the mixture can function to improve flow of the mixture through the extrusion die. Improved flow through the extrusion die can lead to easier equipment start-up, smoother extrusion, faster processing, lower extrusion pressures, and improved product appearance. Extrusion aids, their effective amounts and methods of incorporation into the mixture can be varied and selected according to ordinary skill in the art. Hereafter, the shaped mixture exiting a die, with any composition or any form, will be referred to as the "green extrudate."

Excess water from the green extrudate can be removed by drying to form a dried green extrudate prior to further processing. Conventional methods for drying wet solids can be used to dry the green extrudate, and can include, for example drying in air or an inert gas such as nitrogen or helium. The air or inert gas can be circulating, moving, or static. Drying temperatures can range from about 200° F. to about 400° F., alternatively from about 200° F. to about 300° F., alternatively from about 225° F. to about 275° F. Drying times can range from equal to or greater than about 1 hour, alternatively from about 1 hour to about 10 hours, alternatively from about 2 hours to about 5 hours.

In an embodiment, the dried green extrudate can be calcined to form a calcined extruded catalyst support. Calcination temperatures can range from about 500° F. to about 1500° F., alternatively from about 700° F. to about 1400° F., alternatively from about 850° F. to about 1300° F. Calcination times can range from about 0.5 to about 12 hours, alternatively from about 1 to about 6 hours. In such embodiments, the calcination can be carried out in an oxygen containing atmosphere. As used herein, "dry" air refers to air having a dew point of less than about −40° F. The calcined extruded catalyst support can be directly used in a catalyst preparation or can be further processed according to the following description.

In an embodiment, a method of preparing a selective hydrogenation catalyst comprises contacting a calcined extruded catalyst support of the type disclosed herein with a chlorine-containing compound. The chlorine-containing compound can be a gas, a liquid, or combinations thereof. An embodiment comprises contacting the catalyst support with a liquid chlorine-containing compound to create a chlorided catalyst support. Such a liquid can comprise at least one chlorine-containing compound. In some embodiments, the liquid chlorine-containing compound to which the inorganic catalyst support can be exposed to create the chlorided catalyst support include, but are not limited to, hydrochloric acid; alkaline metal chloride; alkaline earth chloride; chlorohydrocarbons; compounds described by the formula $N(H_vR_wR'_xR''_yR'''_z)Cl$, where R, R', R", and R''' is methyl, ethyl, propyl, butyl, or any combination thereof and v, w, x, y, z can be 0 to 4 provided v+w+x+y+z=4; or combinations thereof. In some embodiments, the alkaline metal chloride can comprise potassium chloride, sodium chloride, lithium chloride, or combinations thereof. In some embodiments, the alkaline earth chloride can comprise calcium chloride, barium chloride, or combinations thereof. In some embodiments, compounds described by the formula $N(H_vR_wR'_xR''_yR'''_z)Cl$ can comprise ammonium chloride, methyl ammonium chloride, tetramethylammonium chloride, tetraethylammonium chloride, or combinations thereof. Chloro-hydrocarbons as used herein can comprise compounds containing 1-10 carbons wherein there is at least one substitution of hydrogen for chlorine. In some embodiments chloro-hydrocarbons comprise compounds described by the formula $CCl_xH_y$, (where x+y=4); compounds described by the formula $C_2Cl_xH_y$, (where x+y=6); or combinations thereof. In some embodiments compounds described by the formula $CCl_xH_y$, comprise carbon tetrachloride, dichloromethane, or combinations thereof. In some embodiments, compounds described by the formula $C_2Cl_xH_y$, comprise trichloroethane. In an embodiment, the liquid chlorine-containing compound comprises potassium chloride in solution.

The calcined extruded catalyst support can be contacted with the liquid chlorine-containing compound in any suitable manner. In an embodiment, the method used to contact a calcined extruded catalyst support with a liquid chlorine-containing compound can be incipient wetness impregnation. During incipient wetness impregnation, the pores of the support become substantially filled with the liquid chlorine-containing compound. Other contacting methods such as soaking can also be employed to contact the calcined extruded catalyst support with the liquid chlorine-containing compound to create a chlorided catalyst support.

An alternative embodiment comprises initially contacting the calcined extruded catalyst support with a gaseous chlorine-containing compound to create a chlorided catalyst support. In some embodiments, the chlorine-containing compounds that can be employed as gases include, but are not limited to, hydrogen chloride gas, chlorine gas, $CCl_xH_y$, (where x+y=4), $C_2Cl_xH_y$, (where x+y=6), or combinations thereof. In another embodiment, the gaseous chlorine-containing compounds are obtained by heating a volatile chloro-hydrocarbon or mixture thereof.

A method used to contact a calcined extruded catalyst support with a gaseous chlorine-containing compound can be accomplished by heating the calcined extruded catalyst support in the presence of a gaseous chlorine-containing compound and optionally in the presence of oxygen, water, nitrogen, hydrogen or mixtures thereof to create a chlorided catalyst support. In an embodiment, the calcined extruded catalyst support can be contacted with a gaseous chlorine-containing compound at temperatures of from about 300° C. to about 850° C. for from about 0.2 to about 20 hours.

The amount of chlorine-containing compound deposited on the calcined extruded catalyst support is controlled independently of the contact method, whether by liquid contacting, gas phase contacting, or combination thereof. The contacting method can deposit an amount of chlorine-containing compound such that the chlorided catalyst support, i.e., the calcined extruded catalyst support after exposure to a chlorine-containing compound, comprises from about 20 wt. % to about 0.001 wt. % chlorine based on a total weight of the chlorided catalyst support, alternatively from about 10 wt. % to about 0.01 wt. % chlorine, alternatively from about 2 wt. % to about 0.05 wt. % chlorine.

After the calcined extruded catalyst support has been contacted with the chlorine-containing compound to create the chlorided catalyst support, the chlorided catalyst support can be removed from contact with the chlorine-containing compound and processed to remove from the chlorided catalyst support unwanted elements such as an amount of chlorine-containing compound, decomposition products thereof, or other unwanted elements to create a clean chlorided catalyst support and otherwise prepare the chlorided catalyst support for further processing to produce a selective hydrogenation catalyst. Removing an amount of chlorine-containing compound and/or any other unwanted elements can occur via a wash, via vaporization, or combinations thereof, depending, for example, on the type of chlorine-containing compound involved. The vaporization can be accomplished at a temperature of from about 300° C. to about 850° C. for from about 0.2 to about 20 hours. After processing, the clean chlorided catalyst support can comprise from about 0 to about 2000 ppm by weight of chlorine; alternatively, can comprise from about 1 to about 1200 ppm by weight of chlorine; alternatively, from about 2 to about 80 ppm by weight of chlorine; alternatively, from about 3 to about 20 ppm, alternatively less than about 2 ppm by weight of chlorine with respect to the support.

In an embodiment, a chlorided catalyst support produced by contact with a liquid chlorine-containing compound can be exposed to an elevated temperature of from about 50° C. to about 850° C. for from about 0.5 to about 20 hours to dry and/or calcine the chlorided catalyst support, thereby producing a cleaned chlorided catalyst support. In some embodiments, an optional washing step can follow the exposure to an elevated temperature. For example, the support can be washed with water at temperatures of from about 20° C. to about 100° C. for from about 1 minute to about 2 hours. In an embodiment, the washing utilizes hot distilled or deionized water and occurs after drying and/or calcining. Following the washing step, the chlorided catalyst support can optionally undergo another exposure to an elevated temperature of from about 50° C. to about 900° C. for from about 0.5 to about 20 hours to remove any unwanted moisture.

In another embodiment, a chlorided catalyst support produced by contact with a gaseous chlorine-containing compound can be cleaned via vaporization or washing or a combination thereof to remove an amount of chlorine-containing compound, decomposition products thereof, or other unwanted elements. In an embodiment, after contacting the catalyst support with the gaseous chlorine-containing compound, flow of the gaseous chlorine-containing compound is stopped, and the gaseous treated chlorided catalyst support can be continued to be heated and/or calcined by exposure to an elevated temperature in the absence of the gaseous chlorine-containing compound to produce a cleaned chlorided catalyst support. Exposure to an elevated temperature can occur in the presence of oxygen, water, nitrogen and mixtures thereof for less than or equal to about 18 hours. This vaporization removal step can be optionally followed by exposing the chlorided catalyst support with a heated stream of gas free of the chlorine-containing compound to further remove any unwanted elements. After processing, the cleaned chlorided catalyst support can comprise from about 0 to about 2000 ppm by weight of chlorine; alternatively, can comprise from about 1 to about 1200 ppm by weight of chlorine; alternatively, from about 2 to about 80 ppm by weight of chlorine; alternatively, from about 3 to about 20 ppm, alternatively less than about 2 ppm by weight of chlorine with respect to the support.

In an embodiment, a method of preparing a hydrogenation catalyst comprises selecting an inorganic support having a multimodal distribution of pore diameters. In an embodiment, at least one distribution of pore diameters comprises pores having a diameter of equal to or greater than about 120 nm. The selected support can then be treated as a catalyst support of the type disclosed herein and subjected to the processing disclosed herein (e.g., drying, calcining, chloriding).

In an embodiment, a method of preparing a selective hydrogenation catalyst comprises contacting a cleaned chlorided catalyst support of the type disclosed herein with at least one catalytically active metal, alternatively palladium. The palladium can be added to the cleaned chlorided catalyst support by contacting the cleaned chlorided catalyst support with a palladium-containing compound to form a palladium supported composition as will be described in more detail later herein. Examples of suitable palladium-containing compounds include without limitation palladium chloride, palladium nitrate, ammonium hexachloropalladate, ammonium tetrachlopalladate, palladium acetate, palladium bromide, palladium iodide, tetraamminepalladium nitrate, or combinations thereof. In an embodiment, the palladium-containing compound is a component of an aqueous solution. An example of palladium-containing solution suitable for use in this disclosure includes without limitation a solution comprising palladium metal.

In an embodiment, palladium is present in the mixture for preparation of a selective hydrogenation catalyst in an amount of from about 0.005 wt. % to about 2 wt. %, alternatively from about 0.005 wt. % to about 1 wt. % or alternatively from about 0.005 wt. % to about 0.5 wt. % based on the total catalyst weight.

In an embodiment, a method of preparing a selective hydrogenation catalyst can initiate with the contacting of cleaned chlorided catalyst support with a palladium-containing compound to form a supported palladium composition. The contacting can be carried out using any suitable technique. For example, the cleaned chlorided catalyst support can be contacted with the palladium-containing compound by soaking, or incipient wetness impregnation of the support with a palladium-containing solution. In such embodiments, the resulting supported palladium composition can have greater than about 90 wt. %, alternatively from about 92 wt. % to about 98 wt. %, alternatively from about 94 wt. % to about 96 wt. % of the palladium concentrated near the periphery of the palladium supported composition, as to form a palladium skin. In an embodiment, the cleaned chloride catalyst support is contacted with the palladium-containing solution by soaking the support in the palladium-containing solution.

The palladium skin can be any thickness as long as such thickness can promote the hydrogenation processes disclosed herein. Generally, the thickness of the palladium skin can be in the range of from about 1 micron to about 3000 microns, alternatively from about 5 microns to about 2000 microns, alternatively from about 10 microns to about 1000 microns, alternatively from about 50 microns to about 500 microns. Examples of such methods are further described in more details in U.S. Pat. Nos. 4,404,124 and 4,484,015, each of which is incorporated by reference herein in its entirety.

Any suitable method can be used for determining the concentration of the palladium in the skin of the palladium supported composition and/or the thickness of the skin. For example, one method involves breaking open a representative sample of the palladium supported composition particles and treating the palladium supported composition particles with a dilute alcoholic solution of N,N-dimethyl-para-nitrosoaniline. The treating solution reacts with the palladium to give a red color that can be used to evaluate the distribution of the palladium. Yet another technique for measuring the concentration of the palladium in the skin of the palladium supported composition involves breaking open a representative sample of catalyst particles, followed by treating the particles with a reducing agent such as hydrogen to change the color of the skin and thereby evaluate the distribution of the palladium. Alternatively, the palladium skin thickness can be determined using electron probe microanalysis.

The supported palladium composition formed by contacting the cleaned chlorided catalyst support with the palladium-containing solution optionally can be dried at a temperature of from about 15° C. to about 150° C., alternatively from about 30° C. to about 100° C., alternatively from about 60° C. to about 100° C.; and for a period of from about 0.1 hour to about 100 hours, alternatively from about 0.5 hour to about 20 hours, alternatively from about 1 hour to about 10 hours. Alternatively, the palladium supported composition can be calcined. This calcining step can be carried out at temperatures up to about 850° C., alternatively of from about 150° C. to about 800° C., alternatively from about 150° C. to about 750° C., alternatively from about 150° C. to about 700° C.; and for a period of from about 0.2 hour to about 20 hours, alternatively from about 0.5 hour to about 20 hours, alternatively from about 1 hour to about 10 hours.

In an embodiment, the selective hydrogenation catalyst can further comprise one or more selectivity enhancers. Suitable selectivity enhancers include, but are not limited to, Group 1B metals, Group 1B metal compounds, silver compounds, fluorine, fluoride compounds, sulfur, sulfur compounds, alkali metals, alkali metal compounds, alkaline metals, alkaline metal compounds, iodine, iodide compounds, or combinations thereof. In an embodiment, the selective hydrogenation catalyst comprises one or more selectivity enhancers which can be present in total in the mixture for preparation of the selective hydrogenation catalyst in an amount of from about 0.001 wt. % to about 10 wt. % based on the total weight of the selective hydrogenation catalyst, alternatively from about 0.01 wt. % to about 5 wt. %, alternatively from about 0.01 wt. % to about 2 wt. %. The amount of selectivity enhancer incorporated into the selective hydrogenation catalyst can be in the range described herein for the amount of selectivity enhancer used to prepare the selective hydrogenation catalyst.

In an embodiment, the selectivity enhancer comprises silver (Ag), silver compounds, or combinations thereof. Examples of suitable silver compounds include without limitation silver nitrate, silver acetate, silver bromide, silver chloride, silver iodide, silver fluoride, or combinations thereof. In an embodiment, the selectivity enhancer comprises silver nitrate. The selective hydrogenation catalyst can be prepared using silver nitrate in an amount of from about 0.005 wt. % to about 5 wt. % silver based on the total weight of the selective hydrogenation catalyst, alternatively from about 0.01 wt. % to about 1 wt. % silver, alternatively from about 0.05 wt. % to about 0.5 wt. %. The amount of silver incorporated into the selective hydrogenation catalyst can be in the range described herein for the amount of silver nitrate used to prepare the selective hydrogenation catalyst.

In an embodiment, the selectivity enhancer comprises alkali metals, alkali metal compounds, or combinations thereof. Examples of suitable alkali metal compounds include without limitation elemental alkali metal, alkali metal halides (e.g., alkali metal fluoride, alkali metal chloride, alkali metal bromide, alkali metal iodide), alkali metal oxides, alkali metal carbonate, alkali metal sulfate, alkali metal phosphate, alkali metal borate, or combinations thereof. In an embodiment, the selectivity enhancer comprises potassium fluoride (KF). In another embodiment, the selective hydrogenation catalyst is prepared using an alkali metal compound in an amount of from about 0.01 wt. % to about 5 wt. % based on the total weight of the selective hydrogenation catalyst, alternatively from about 0.03 wt. % to about 2 wt. %, alternatively from about 0.05 wt. % to about 1 wt. %. The amount of alkali metal incorporated into the selective hydrogenation catalyst can be in the range described herein for the amount of alkali metal compound used to prepare the selective hydrogenation catalyst.

In some embodiments, one or more selectivity enhancers of the type described previously herein can be added to the supported palladium composition. In an embodiment, silver can be added to the supported palladium composition. For example, the supported palladium composition can be placed in an aqueous silver nitrate solution of a quantity greater than that necessary to fill the pore volume of the composition. The resulting material is a palladium/silver supported composition (herein this particular embodiment of the selective hydrogenation catalyst is referred to as a Pd/Ag composition). The Pd/Ag composition may be dried and/or calcined as previously described herein.

In an embodiment, one or more alkali metals can be added to the Pd/Ag composition using any suitable technique such as those described previously herein. In an embodiment, the selectivity enhancer comprises potassium fluoride, and the resulting material is a palladium/silver/alkali metal fluoride supported composition (herein this particular embodiment of the selective hydrogenation catalyst is referred to as a Pd/Ag/KF composition).

In an embodiment, the supported palladium composition is contacted with both an alkali metal halide and a silver compound. Contacting the supported palladium composition with both an alkali metal halide and a silver compound can be carried out simultaneously; alternatively the contacting can be carried out sequentially in any user-desired order.

In an embodiment, a selective hydrogenation catalyst formed in accordance with the methods disclosed herein comprises an α-alumina support of the type disclosed herein, palladium, and one or more selectivity enhancers, (e.g., silver and/or potassium fluoride). The selective hydrogenation catalyst (Pd/Ag, Pd/KF, and/or the Pd/Ag/KF/ compositions) can be dried to form a dried selective hydrogenation catalyst. In some embodiments, this drying step can be carried out at a temperature in the range of from about 0° C. to about 150° C., alternatively from about 30° C. to about 100° C., alternatively from about 50° C. to about 80° C.; and for a period of from about 0.1 hour to about 100 hours, alternatively from about 0.5 hour to about 20 hours, alternatively from about 1 hour to about 10 hours.

The dried selective hydrogenation catalyst can be reduced using hydrogen gas or a hydrogen gas containing feed, e.g., the feed stream of the selective hydrogenation process, thereby providing for optimum operation of the selective hydrogenation process. Such a gaseous hydrogen reduction can be carried out at a temperature in the range of from, for example, about 0° C. to about 400° C., alternatively 20° C. to about 300° C., or alternatively about 30° C. to about 250° C.

In an embodiment, a selective hydrogenation catalyst of the type disclosed herein can catalyze a selective hydrogenation process. In some embodiments a selective hydrogenation catalyst of the type disclosed herein is used in conjunction with one or more conventional hydrogenation catalysts to catalyze a selective hydrogenation process. In such embodiments having a conventional hydrogenation catalyst and a selective hydrogenation catalyst of the type disclosed herein, the selective hydrogenation catalyst may be present in an amount that comprises greater than about 50% of the total amount of hydrogenation catalyst present during the selective hydrogenation process. Alternatively greater than about 70% or alternatively greater than about 85%. Herein, the phrase "conventional hydrogenation catalysts" refers to hydrogenation catalysts that lack a catalyst support of the type disclosed herein.

The selective hydrogenation catalyst can be contacted with an unsaturated hydrocarbon stream primarily containing unsaturated hydrocarbons, e.g., ethylene, but also containing a highly unsaturated hydrocarbon, e.g., acetylene. The contacting can be executed in the presence of hydrogen at conditions effective to selectively hydrogenate the highly unsaturated hydrocarbon to an unsaturated hydrocarbon. In an embodiment, the selective hydrogenation catalysts of the type disclosed herein are used in the hydrogenation of highly unsaturated hydrocarbons such as for example and without limitation acetylene, methylacetylene, propadiene, butadiene or combinations thereof. As used herein, a highly unsaturated hydrocarbon is defined as a hydrocarbon containing a triple bond, two conjugated carbon-carbon double bonds, or two cumulative carbon-carbon double bonds. As used herein, an unsaturated hydrocarbon is defined as a hydrocarbon containing an isolated carbon-carbon double bond. FIG. 1 illustrates an embodiment of a hydrogenation process that utilizes a selective hydrogenation catalyst of the type disclosed herein. The hydrogenation process includes feeding an unsaturated hydrocarbon stream 10 and a hydrogen ($H_2$) stream 20 to a hydrogenation reactor 30 within which the selective hydrogenation catalyst is disposed. The unsaturated hydrocarbon stream 10 primarily comprises one or more unsaturated hydrocarbons, but it can also contain one or more highly unsaturated hydrocarbons such as for example and without limitation acetylene, methylacetylene, propadiene, and butadiene. Alternatively, unsaturated hydrocarbon stream 10 and hydrogen stream 20 can be combined in a single stream that is fed to hydrogenation reactor 30.

In an embodiment, reactor 30 is a selective hydrogenation reactor that can belong to an acetylene removal unit of an unsaturated hydrocarbon production plant in a backend configuration. As used herein, "backend" refers to the location of the acetylene removal unit in an unsaturated hydrocarbon production unit that receives the lower boiling fraction from a deethanizer fractionation tower that receives the higher boiling fraction from a demethanizer fractionation tower which receives a feed from an unsaturated hydrocarbon production process.

In an embodiment, reactor 30 is a selective hydrogenation reactor that can belong to an acetylene removal unit of an unsaturated hydrocarbon production plant in a frontend deethanizer configuration. As used herein, "frontend deethanizer" refers to the location of the acetylene removal unit in an unsaturated hydrocarbon production unit that receives the lower boiling fraction from a deethanizer fractionation tower that receives a feed from an unsaturated hydrocarbon production process.

In an embodiment, reactor 30 is a selective hydrogenation reactor that may belong to an acetylene removal unit of an unsaturated hydrocarbon production plant in a frontend depropanizer configuration. As used herein, "frontend depropanizer" refers to the location of the acetylene removal unit in an unsaturated hydrocarbon production unit that receives the lower boiling fraction from a depropanizer fractionation tower that receives a feed from an unsaturated hydrocarbon production process.

In an embodiment, reactor 30 is a selective hydrogenation reactor that can belong to an acetylene removal unit of an unsaturated hydrocarbon production plant in a raw gas configuration. As used herein, "raw gas" refers to the location of the acetylene removal unit in an unsaturated hydrocarbon production unit that receives a feed from an unsaturated hydrocarbon production process without any intervening hydrocarbon fractionation.

It is understood that hydrogenation reactor 30, and likewise the selective hydrogenation catalysts disclosed herein, are not limited to use in backend acetylene removal units, frontend deethanizer units, frontend depropanizer, or raw gas units and can be used in any process wherein a highly unsaturated hydrocarbons contained within an unsaturated hydrocarbon stream is selectively hydrogenated to a unsaturated hydrocarbon. In frontend deethanizer units, frontend depropanizer, or raw gas units, the unsaturated hydrocarbon stream 10 contains sufficient quantities of hydrogen for the hydrogenation reaction, and a hydrogen stream 20 may become unnecessary for the reaction.

In those embodiments wherein the acetylene removal unit is in a backend configuration, the highly unsaturated hydrocarbon being fed to the hydrogenation reactor 30 comprises acetylene. The mole ratio of the hydrogen to the acetylene being fed to hydrogenation reactor 30 can be in the range of from about 0.1 to about 10, alternatively from about 0.2 to about 5, alternatively from about 0.5 to about 4.

In those embodiments wherein the acetylene removal unit is in a front end deethanizer, front-end depropanizer or raw gas configuration, the highly unsaturated hydrocarbon being fed to the hydrogenation reactor 30 comprises acetylene. In such an embodiment, the mole ratio of the hydrogen to the acetylene being fed to the hydrogenation reactor 30 can be in the range of from about 10 to about 3000, alternatively from about 10 to about 2000, alternatively from about 10 to about 1500.

In those embodiments wherein the acetylene removal unit is in a front-end depropanizer or raw gas configuration, the highly unsaturated hydrocarbon being fed to the hydrogenation reactor 30 comprises methylacetylene. In such an embodiment, the mole ratio of the hydrogen to the methylacetylene being fed to the hydrogenation reactor 30 can be in the range of from about 3 to about 3000, alternatively from about 5 to about 2000, alternatively from about 10 to about 1500.

In those embodiments wherein the acetylene removal unit is in a front-end depropanizer or raw gas configuration, the highly unsaturated hydrocarbon being fed to the hydrogenation reactor 30 comprises propadiene. In such an embodiment, the mole ratio of the hydrogen to the propadiene being fed to the hydrogenation reactor 30 can be in the range of from about 3 to about 3000, alternatively from about 5 to about 2000, alternatively from about 10 to about 1500.

In another embodiment, reactor 30 can represent a plurality of reactors. The plurality of reactors can optionally be separated by a means to remove heat produced by the reaction. The plurality of reactors can optionally be separated by a means to control inlet and effluent flows from reactors or heat removal means allowing for individual or alternatively groups of reactors within the plurality of reactors to be regenerated. The selective hydrogenation catalyst can be arranged in any suitable configuration within hydrogenation reactor 30, such as a fixed catalyst bed. Carbon monoxide can also be fed to reactor 30 via a separate stream (not shown), or it can be combined with hydrogen stream 20. In an embodiment, the amount of carbon monoxide being fed to reactor 30 during the hydrogenation process is less than about 0.15 mole percent (mol. %) based on the total moles of fluid being fed to reactor 30.

Hydrogenation reactor 30 can be operated at conditions effective to selectively hydrogenate highly unsaturated hydrocarbons to one or more unsaturated hydrocarbons upon contacting the selective hydrogenation catalyst in the presence of the hydrogen. The conditions are desirably effective to maximize hydrogenation of highly unsaturated hydrocarbons to unsaturated hydrocarbons and to minimize hydrogenation of highly unsaturated hydrocarbons to saturated hydrocarbons. In some embodiments, acetylene can be selectively hydrogenated to ethylene. Alternatively methylacetylene can be selectively hydrogenated to propylene; alternatively propadiene can be selectively hydrogenated to propylene. Alternatively, butadiene can be selectively hydrogenated to butenes. In some embodiments, the temperature within the hydrogenation zone can be in the range of from about 5° C. to about 300° C., alternatively from about 10° C. to about 250° C., alternatively from about 15° C. to about 200° C. In some embodiments, the pressure within the hydrogenation zone can be in the range of from about 15 (204 kPa) to about 2,000 (13,890 kPa) pounds per square inch gauge (psig), alternatively from about 50 psig (446 kPa) to about 1,500 psig (10,443 kPa), alternatively from about 100 psig (790 kPa) to about 1,000 psig (6,996 kPa).

Referring back to FIG. 1, an effluent stream 40 comprising unsaturated hydrocarbons, including the one or more monoolefins produced in hydrogenation reactor 30, and any unconverted reactants exit hydrogenation reactor 30. In an embodiment where hydrogenation reactor 30 is in a backend acetylene removal unit configuration, effluent stream 40 primarily comprises ethylene comprises less than about 5 ppm, alternatively less than about 1 ppm of highly unsaturated hydrocarbons. In embodiments wherein hydrogenation reactor 30 is in a frontend deethanizer, frontend depropanizer, or raw gas acetylene removal unit configuration, effluent stream 40 primarily comprises ethylene comprises less than about 5 ppm, alternatively less than about 1 ppm of acetylene, while other highly unsaturated hydrocarbons such as methylacetylene or propadiene comprises less than about 5000 ppm, alternatively less than about 4000 ppm.

In an embodiment, a selective hydrogenation catalyst of the type described herein can have a comparable catalytic activity when compared to an otherwise similar catalyst lacking a catalyst support of the type described herein. For example, a selective hydrogenation catalyst of this disclosure can have at least one performance property that is improved when compared to an otherwise similar catalyst. In an embodiment, a selective hydrogenation catalyst of this disclosure has an optimal balance of desirable properties. For example, a selective hydrogenation catalyst of the type disclosed herein has a catalytic activity or clean up temperature comparable to an otherwise similar catalyst. The comparable catalytic activity can translate to a comparable clean up temperature. Hereinafter, an otherwise similar catalyst refers to a selective hydrogenation catalyst comprising an inorganic catalyst support, palladium and one or more selectivity enhancers but lack a catalyst support of the type disclosed herein. Herein, the cleanup temperature is referred to as T1 and refers to the temperature at which the acetylene concentration drops below 20 ppm in the effluent when processing a representative frontend deethanizer, frontend depropanizer, or raw gas acetylene removal unit feed stream comprising unsaturated hydrocarbon and highly unsaturated hydrocarbons such as acetylenes and diolefins. Determinations of T1 are described in more detail for example in U.S. Pat. Nos. 7,417,007 and 6,417,136, each of which are incorporated herein in their entirety. In an embodiment, a selective hydrogenation catalyst of the type disclosed herein can have a T1 of from about 80° F. to about 160° F., alternatively from about 85° F. to about 150° F., alternatively from about 90° F. to about 140° F. for fresh catalyst. In an embodiment, a selective hydrogenation catalyst of the type described herein can display a selectivity window that is increased when compared to an otherwise similar catalyst lacking a catalyst support of the type described herein. Herein, a selectivity window refers to the reaction time period over which the catalyst displays a desired selectivity for a specified reaction. For example, a selective hydrogenation catalyst of the type disclosed herein when employed as a catalyst in acetylene hydrogenation reactors can display a selectivity window for ethylene of equal to or greater than about 200 hours, alternatively equal to or greater than about 250 hours, or alternatively equal to or greater than about 300 hours. The selectivity window of selective hydrogenation catalysts of the type disclosed herein can be increased by equal to or greater than about 50%, alternatively equal to or greater than about 75%, or alternatively equal to or greater than about 100% when compared to an otherwise similar catalyst lacking a catalyst support of the type disclosed herein. Alternatively, the selectivity window of selective hydrogenation catalysts of the type disclosed herein can be increased by equal to or greater than about 50%, alternatively equal to or greater than about 75%, or alternatively equal to or greater than about 100% when compared to an otherwise identical catalyst lacking a catalyst support of the type disclosed herein.

In an embodiment, a selective hydrogenation catalyst of the type disclosed herein can have an operating window of from about 35° F. to about 120° F., alternatively from about 40° F. to about 80° F., or alternatively from about 45° F. to about 60° F. The operating window of a selective hydrogenation catalyst of the type described herein can be increased by greater than about 10%, alternatively greater than about 15%, alternatively greater than about 20% when compared to an otherwise similar catalyst prepared in the absence of catalyst support of the type described herein. Alternatively, the operating window of a selective hydrogenation catalyst of the type described herein can be increased by greater than about 10%, alternatively greater than about 15%, alternatively greater than about 20% when compared to an otherwise identical catalyst prepared in the absence of catalyst support of the type described herein. An operating window (AT) is defined as the difference between a runaway temperature (T2) at which 3 wt. % of ethylene is hydrogenated from a feedstock comprising highly unsaturated and unsaturated hydrocarbons, and the cleanup temperature (T1). AT is a convenient measure of the catalysts selectivity window and operation stability in the hydrogenation of highly unsaturated hydrocarbons (e.g., acetylene) to unsaturated hydrocarbons (e.g., ethylene). The more selective a catalyst, the higher the temperature beyond T1 required to hydrogenate a given unsaturated hydrocarbons (e.g., ethylene). The T2 is coincident with the temperature at which a high probability of runaway ethylene hydrogenation reaction could exist in an adiabatic reactor. Therefore, a larger AT translates to a more selective catalyst and a wider operation window for the complete acetylene hydrogenation.

In an embodiment a method comprises providing a catalyst support of the type disclosed herein and utilizing the catalyst support to form a selective hydrogenation catalyst. The selective hydrogenation catalyst can be further processed into a packaged product containing or associated with written material. In some embodiments, the written material can provide information on the selectivity window of a selective hydrogenation catalyst formed from a catalyst support of the type disclosed herein alone or in comparison to a selective hydrogenation catalyst prepared in the absence of a catalyst support of the type disclosed herein. In some embodiments, the written material can provide instructions and/or recommendations for utilization of the selective hydrogenation catalyst in one or more applications. For example, the written material can indicate the selective hydrogenation catalyst formed from a catalyst support of the type disclosed herein (e.g., having a bimodal distribution of pore diameters) is suitable for use in applications where a broader selectivity window is desirable.

EXAMPLES

The disclosure having been generally described, the following examples are given as particular embodiments of the disclosure and to demonstrate the practice and advantages thereof. It is understood that the examples are given by way of illustration and are not intended to limit the specification of the claims to follow in any manner.

Example 1

This example illustrates the preparation of various palladium-containing catalyst compositions to be used in a hydrogenation process. Catalysts A thru E were prepared as follows: The α-alumina support having a surface area ranging from 5 $m^2/g$ to 12 $m^2/g$ was supplied by BASF. The support was then chloride-treated, followed by the addition of palladium and silver as described herein. Tables 1, 2, and 3 summarize the physical properties of catalysts A thru E. FIGS. 2-6 show the pore size distribution from mercury pore symmetry for catalysts A thru E. The dashed lines represent the sample distributions while the solid line represents percentage cumulative intrusion.

TABLE 1

| Catalyst | Form | Pd (ppm) | Ag (ppm) | Surface Area $(m^2/g)$[1] |
|---|---|---|---|---|
| A | pellet | 252 | 1718 | 9.57 |
| B | extrudate | 284 | 2492 | 8.12 |
| C | extrudate | 308 | 1869 | 8.57 |
| D | pellet | 267 | 1840 | 6.71 |
| E | extrudate | 307 | 1889 | 11.22 |

Pellets were ~4 mm × 4 mm extrudates were ~5 mm × 3 mm
[1]By Brunauer, Emmett, and Teller method

TABLE 2

| | RANGE 1 | | RANGE 2 | | RANGE 3 | | RANGE 4 | |
|---|---|---|---|---|---|---|---|---|
| Catalyst | Pore size Diameter range (nm) | % total pore volume | Pore size Diameter range (nm) | % total pore volume | Pore size Diameter range (nm) | % total pore volume | Pore size Diameter range (nm) | % total pore volume |
| A | 29736 to 2000 | 0.51 | — | — | 2000 to 45 | 94.29 | 45 to 10 | 5.2 |
| B | 21409 to 2,000 | 0.15 | 2000 to 332 | 19.32 | 332 to 35 | 80.53 | — | — |
| C | 21449 to 230 | 24.7 | — | — | 230 to 30 | 74.56 | 30 to 10 | 0.74 |
| D | 21464 to 280 | 23.9 | — | — | 280 to 30 | 76.1 | — | — |
| E | 21469 to 280 | 17.53 | — | — | 280 to 36 | 76.87 | 36 to 10 | 5.6 |

TABLE 3

| Catalyst | Form | Surface Area $(m^2/g)$[1] | Pore volume $(cc/g)$[2] |
|---|---|---|---|
| A | pellet | 9.57 | 0.326 |
| B | extrudate | 8.12 | 0.344 |
| C | extrudate | 8.57 | 0.253 |
| D | pellet | 6.71 | 0.212 |
| E | extrudate | 11.22 | 0.265 |

[1]By Brunauer, Emmett, and Teller method
[2]By ASTM UOP578-02

Example 2

Figure 7:
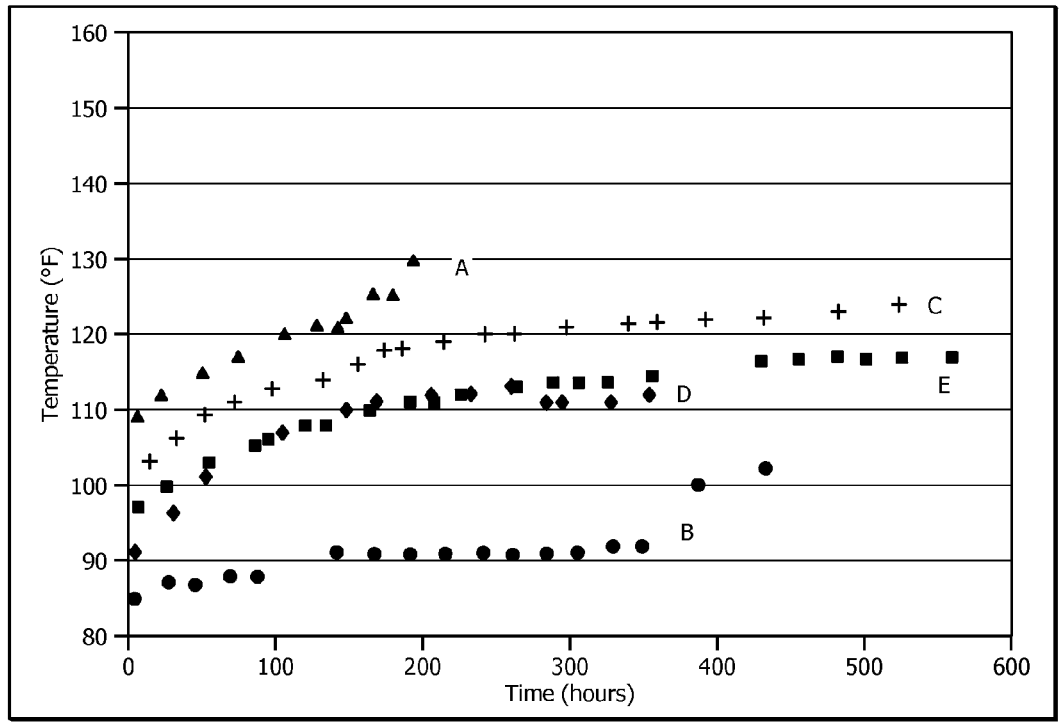
FIG. 7 is a plot of the temperature necessary to maintain a 90% conversion of acetylene as a function of time for the samples from Example 1.
Figure 8:
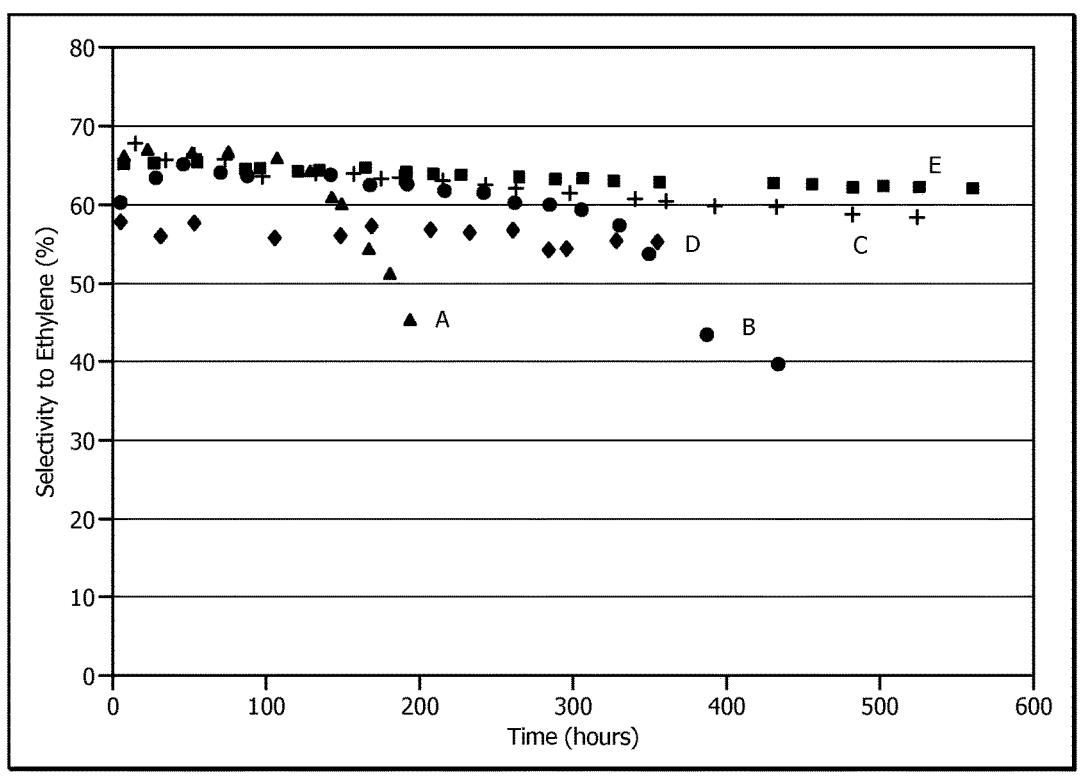
FIG. 8 is a plot of the ethylene selectivity as a function of time for the samples from Example 1.

Catalyst performance runs were made as follows: About 20 mL of catalyst was mixed with 40 mL of alundum and placed in a stainless steel jacketed reactor tube having a 0.692 inch inner diameter and a length of about 18 inches. The catalyst resided in the middle of the reactor and both ends of the reactor were packed with about 10 mL of alundum. The reaction temperature was controlled by circulating ethylene glycol through the jacket of the reactor tube. The catalyst was then activated with hydrogen at a flowrate of 200 mL/min at atmospheric pressure at the listed temperature for two hours. The catalyst was then contacted with the feed gas (approximately: 13 wt. % methane, 85.8 wt. % ethylene, 1.2 wt. % acetylene, and 0.1 wt. % hydrogen) at about 913 mL/min at 200 psig. Some runs used a higher hydrogen concentration and are noted likewise. The reaction temperature was adjusted to yield an acetylene conversion of about 90%. Conversion is referred to as the disappearance of acetylene. Gas analysis was performed by gas chromatography using a KCl—Al$_2$O$_3$ PLOT column. FIG. 7 shows the temperature needed to maintain a 90% conversion of acetylene as a function of time. FIG. 8 shows the selectivity to ethylene as a function of time.

The selectivity (sel.) to ethylene was also calculated using the following set of equations, where "C$_4$" represents butane, butenes and butadiene and where "heavies" refer to hydrocarbons having more carbon atoms than C$_4$:

selectivity to ethane=(weight of ethane made/weight of acetylene consumed)*100 selectivity to C$_4$'s=(weight of C$_4$'s made/weight of acetylene consumed)*100 selectivity to heavies=(weight of heavies made/weight of acetylene consumed)*100 selectivity to ethylene=100–sel. to ethane–sel. to C$_4$'s–sel. to heavies

The results demonstrate that while all the catalysts displayed good activity as indicated by the comparable temperatures at time zero, catalysts of the type disclosed herein (i.e., catalysts C, D, and E) displayed a leveling of the adjusted temperature, FIG. 7. This in contrast to catalysts A and B which do not have a catalyst support with a pore distribution of the type disclosed herein. In the case of catalysts A and B, the temperature begins to increase toward the end of the run. Further, referring to FIG. 8, with regards to selectivity catalysts C, D, and E displayed an increased selectivity as indicated by a plateau in selectivity over the time period investigated. In contrast, catalysts A and B show a decline in selectivity after about 150 hours. Catalysts C, D, and E are selective hydrogenation catalysts having a pore size distribution, specifically the presence of the peak around 1,000 nm in the pore size distribution while catalysts A and B do not have this peak.

ADDITIONAL EMBODIMENTS

The following enumerated embodiments are provided as non-limiting examples:

1. A composition comprising:
   an extruded inorganic support comprising an oxide of a metal or metalloid; and at least one catalytically active metal,
   wherein the extruded inorganic support has pores, a total pore volume, and a pore size distribution; wherein the pore size distribution displays at least two peaks of pore diameters, each peak having a maximum; wherein a first peak has a first maximum of pore diameters of equal to or greater than about 120 nm and a second peak has a second maximum of pore diameters of less than about 120 nm; and wherein greater than or equal to about 5% of a total pore volume of the extruded inorganic support is contained within the first peak of pore diameters.
2. The composition of embodiment 1 wherein the first maximum of the first peak of pore diameters is from about 200 nm to about 9000 nm.
3. The composition of embodiment 1 or 2 wherein greater than or equal to about 10% of the total pore volume of the extruded inorganic support is contained within the first peak of pore diameters.
4. The composition of embodiment 1 or 3 wherein the first maximum of the first peak of pore diameters is from about 400 nm to about 8000 nm.
5. The composition of embodiment 4 wherein greater than or equal to about 15% of the total pore volume of the extruded inorganic support is contained within the first peak of pore diameters.
6. The composition of any preceding embodiment wherein the oxide of a metal or metalloid consists essentially of silica, titania, alumina, or aluminate.
7. The composition of embodiment 1, 2, 3, 4, or 5 wherein the oxide of a metal or metalloid consists essentially of a spinel.
8. The composition of any preceding embodiment having a surface area of from about 1 m2/g to about 35 m$^2$/g.
9. The composition of any preceding embodiment having a total pore volume of from about 0.1 cc/g to about 0.6 cc/g as determined by differential mercury intrusion.
10. The composition of any preceding embodiment wherein the distance between the first maximum of the first peak and the second maximum of the second peak is at least about 400 nm.
11. The composition of any preceding embodiment wherein the first peak is non-Gaussian and has a peak width at half height that is greater than the peak width at half height of the second peak.
12. The composition of any preceding embodiment further comprising a halide.
13. The composition of any preceding embodiment further comprising a Group 10 metal.
14. The composition of any preceding embodiment further comprising a Group 1B metal.
15. The composition of any preceding embodiment further comprising chloride.
16. A method of preparing a hydrogenation catalyst comprising:
   extruding a mixture comprising an oxide of a metal or metalloid, a pore former, and water to form an extrudate;
   drying the extrudate to form a dried extrudate;
   calcining the dried extrudate to from a calcined extrudate;
   contacting the calcined extrudate with a chlorine-containing compound to form a chlorided support;
   reducing the amount of chloride in the chlorided support to form a cleaned chlorided support; and
   contacting the cleaned chlorided support with a Group 10 metal and a Group 1B metal to form a hydrogenation catalyst,
   wherein a pore size distribution for the hydrogenation catalyst displays at least two peaks of pore diameters, each peak having a maximum, and wherein a first peak has a first maximum of pore diameters that is equal to or greater than about 120 nm and a second peak has a second maximum of pore diameters that is less than about 120 nm.
17. The method of embodiment 16 wherein the calcined extrudate, the chlorided support, the cleaned chlorided support, or the hydrogenation catalyst has a surface area of from about 1 m$^2$/g to about 35 m$^2$/g.
18. The method of embodiment 16 or 17 wherein the calcined extrudate, the chlorided support, the washed chlorided support, or the hydrogenation catalyst has a total pore volume of from about 0.1 cc/g to about 0.6 cc/g as determined by differential mercury intrusion.
19. The method of embodiment 16, 17, or 18 wherein the extrudate consists essentially of silica, titania, alumina, or aluminate.

20. The method of embodiment 16, 17, or 18 wherein the extrudate consists essentially of alpha alumina.

21. The method of embodiment 16, 17, 18, 19, or 20 wherein greater than or equal to 5% of a total pore volume of the hydrogenation catalyst is contained within the first peak of pore diameters.

22. An extruded inorganic support comprising an oxide of a metal or metalloid, wherein a pore size distribution for the extruded inorganic support displays at least two peaks of pore diameters, each peak having a maximum; wherein a first peak has a first maximum of pore diameters of equal to or greater than about 120 nm and a second peak has a second maximum of pore diameters of less than about 120 nm; wherein greater than or equal to 15% of a total pore volume of the extruded inorganic support is contained within the first peak of pore diameters; and wherein the inorganic support has a surface area of from about 5 $m^2/g$ to about 15 $m^2/g$.

23. A method of preparing a hydrogenation catalyst comprising:
  selecting an inorganic support having a multimodal distribution of pore diameters, wherein at least one distribution of pore diameters comprises pores having a diameter of equal to or greater than about 120 nm;
  extruding a mixture comprising the inorganic support and water to form an extrudate;
  drying the extrudate to form a dried extrudate;
  calcining the dried extrudate to from a calcined extrudate; and
  contacting the calcined extrudate with a Group VIII metal and a Group 1B metal to form a hydrogenation catalyst.

24. The method of embodiment 23 further comprising contacting the calcined extrudate with a chlorine-containing compound to form a chlorided support; contacting the chlorided support with a wash solution to form a washed chlorided support; contacting the washed chlorided support with the Group VIII metal and the Group 1B metal to form the hydrogenation catalyst.

25. A method for selectively hydrogenating a highly unsaturated hydrocarbon to a less unsaturated hydrocarbon in an olefin rich hydrocarbon stream comprising introducing into a reactor a hydrocarbon fluid stream comprising a highly unsaturated hydrocarbon in the presence of hydrogen and a catalyst composition under conditions effective to convert the highly unsaturated hydrocarbon to a less unsaturated hydrocarbon,
  wherein at least 50% of the catalyst composition comprises the hydrogenation catalyst produced according to embodiment 23.

26. A method comprising:
  preparing a plurality of extruded inorganic supports consisting essentially of silica, titania,
  alumina, or a spinel;
  plotting the pore diameter as a function of a log of differential mercury intrusion for the extruded inorganic support; and
  identifying the extruded inorganic supports having at least two peaks, each peak having a maximum, wherein a first peak comprises pores with a first pore diameter maximum equal to or greater than about 120 nm, and wherein the first peak of pore diameters represents greater than or equal to about 5% of a total pore volume of the extruded inorganic support.

27. The method of embodiment 26 further comprising marketing the extruded inorganic supports for use in preparing a selective hydrogenation catalyst.

28. A hydrogenation catalyst comprising a Group 10 metal, a Group 1B metal and at least one of the identified extruded inorganic supports of any preceding embodiment.

29. A packaged product comprising least one of the identified extruded inorganic supports of any preceding embodiment and written material describing use of the identified extruded inorganic supports in the preparation of hydrogenation catalysts having a reduced fouling rate.

While embodiments of the invention have been shown and described, modifications thereof can be made by one skilled in the art without departing from the spirit and teachings of the invention. The embodiments described herein are exemplary only, and are not intended to be limiting. Many variations and modifications of the invention disclosed herein are possible and are within the scope of the invention. Where numerical ranges or limitations are expressly stated, such express ranges or limitations should be understood to include iterative ranges or limitations of like magnitude falling within the expressly stated ranges or limitations (e.g., from about 1 to about 10 includes, 2, 3, 4, etc.; greater than 0.10 includes 0.11, 0.12, 0.13, etc.). Use of the term "optionally" with respect to any element of a claim is intended to mean that the subject element is required, or alternatively, is not required. Both alternatives are intended to be within the scope of the claim. Use of broader terms such as comprises, includes, having, etc. should be understood to provide support for narrower terms such as consisting of, consisting essentially of, comprised substantially of, etc.

Accordingly, the scope of protection is not limited by the description set out above but is only limited by the claims which follow, that scope including all equivalents of the subject matter of the claims. Each and every claim is incorporated into the specification as an embodiment of the present invention. Thus, the claims are a further description and are an addition to the embodiments of the present invention. The disclosures of all patents, patent applications, and publications cited herein are hereby incorporated by reference, to the extent that they provide exemplary, procedural or other details supplementary to those set forth herein.

What is claimed is:

1. A composition comprising:
  an inorganic support comprising an oxide of a metal or metalloid;
  a halide; and
  at least one catalytically active metal,
  wherein the inorganic support has pores, a total pore volume, and a pore size distribution;
  wherein the pore size distribution displays at least two peaks of pore diameters, each peak having a maximum; wherein a first peak has a first maximum of pore diameters of from greater than 1,000 nm to about 6,000 nm; wherein a second peak has a second maximum of pore diameters of less than about 120 nm; and wherein greater than or equal to about 15% of the total pore volume of the inorganic support is contained within the first peak of pore diameters.

2. The composition of claim 1, wherein the inorganic support is an extruded inorganic support.

3. The composition of claim 1, wherein the inorganic support is an agglomerated inorganic support.

4. The composition of claim 1, wherein the oxide of a metal or metalloid consists essentially of silica, titania, alumina, or aluminate.

5. The composition of claim 1 wherein the oxide of a metal or metalloid consists essentially of a spinel.

6. The composition of claim 1, having a total pore volume of from about 0.1 cc/g to about 0.6 cc/g as determined by differential mercury intrusion.

7. The composition of claim 6, wherein the inorganic support has a surface area of from about 3 m²/g to about 27 m²/g.

8. The composition of claim 1, wherein the first peak is non-Gaussian and has a peak width at half height that is greater than the peak width at half height of the second peak.

9. The composition of claim 1, further comprising a Group 10 metal.

10. The composition of claim 1, further comprising a Group 1B metal.

11. The composition of claim 1, wherein the halide is chloride.

12. The composition of claim 1, wherein the at least one catalytically active metal comprises palladium and silver; the halide comprises chloride; and the oxide of a metal or metalloid comprises α-alumina.

13. The composition of claim 1, wherein the at least one catalytically active metal comprises palladium and the palladium is present in the composition in an amount of from about 0.005 wt. % to about 2 wt. % based on the total weight of the composition.

14. The composition of claim 13 wherein greater than about 90 wt. % of the palladium is concentrated near the periphery of the composition.

15. A method of preparing a hydrogenation catalyst comprising:
   forming a mixture comprising an oxide of a metal or metalloid, a pore former, and water;
   drying the mixture to form a dried mixture;
   calcining the dried mixture to from a calcined mixture;
   contacting the calcined mixture with a halide-containing compound to form a halided support;
   reducing the amount of halide in the halided support to form a cleaned halided support; and
   contacting the cleaned hatided support with a Group 10 metal and a Group 1B metal to form a hydrogenation catalyst,
   wherein a pore size distribution for the hydrogenation catalyst displays at least two peaks of pore diameters, each peak having a maximum, wherein a first peak has a first maximum of pore diameters of from greater than 1,000 nm to about 6,000 nm, wherein a second peak has a second maximum of pore diameters of less than about 120 nm, and wherein greater than or equal to about 15% of a total pore volume of the hydrogenation catalyst is contained within the first peak of pore diameters.

16. The method of claim 15, wherein the forming the mixture comprises extruding the mixture to form an extrudate.

17. The method of claim 15, wherein the forming the mixture comprises agglomerating the mixture to form an agglomerate.

18. The method of claim 15, wherein the hydrogenation catalyst has a total pore volume of from about 0.1 cc/g to about 0.6 cc/g as determined by differential mercury intrusion.

19. The method of claim 18, wherein the hydrogenation catalyst has a surface area of from about 3 m²/g to about 27 m²/g.

20. The method of claim 15, wherein the halide is chloride.

21. The method of claim 15, wherein the Group 10 metal comprises palladium; the Group 1B metal comprises silver; the halide comprises chloride; and the oxide of a metal or metalloid comprises α-alumina.

22. A method for selectively hydrogenating a highly unsaturated hydrocarbon to a less unsaturated hydrocarbon in an olefin rich hydrocarbon stream comprising introducing into a reactor a hydrocarbon fluid stream comprising a highly unsaturated hydrocarbon in the presence of hydrogen and a catalyst composition under conditions effective to convert the highly unsaturated hydrocarbon to a less unsaturated hydrocarbon, wherein at least 50% of the catalyst composition comprises the hydrogenation catalyst produced according to claim 15.

23. The method of claim 22, wherein the Group 10 metal comprises palladium; the Group 1B metal comprises silver; the halide comprises chloride; and the oxide of a metal or metalloid comprises α-alumina.

* * * * *